(12) United States Patent
Dobrowolski et al.

(10) Patent No.: US 12,076,428 B2
(45) Date of Patent: Sep. 3, 2024

(54) LIQUID PEARLESCENT COMPOSITION

(71) Applicant: RHODIA OPERATIONS, Aubervilliers (FR)

(72) Inventors: David Dobrowolski, Robbinsville, NJ (US); Cadie Martin, Southampton, PA (US)

( * ) Notice: Subject to any disclaimer, the term of this patent is extended or adjusted under 35 U.S.C. 154(b) by 228 days.

(21) Appl. No.: 17/099,390

(22) Filed: Nov. 16, 2020

(65) Prior Publication Data

US 2021/0169761 A1    Jun. 10, 2021

Related U.S. Application Data

(60) Provisional application No. 62/944,075, filed on Dec. 5, 2019.

(51) Int. Cl.

| | | |
|---|---|---|
| *C11D 3/00* | (2006.01) | |
| *A61K 8/02* | (2006.01) | |
| *A61K 8/20* | (2006.01) | |
| *A61K 8/34* | (2006.01) | |
| *A61K 8/37* | (2006.01) | |
| *A61K 8/41* | (2006.01) | |
| *A61K 8/46* | (2006.01) | |
| *A61Q 5/02* | (2006.01) | |
| *A61Q 19/00* | (2006.01) | |

(52) U.S. Cl.
CPC .............. *A61K 8/37* (2013.01); *A61K 8/0204* (2013.01); *A61K 8/20* (2013.01); *A61K 8/342* (2013.01); *A61K 8/416* (2013.01); *A61K 8/463* (2013.01); *A61Q 5/02* (2013.01); *A61Q 19/00* (2013.01); *A61K 2800/30* (2013.01); *A61K 2800/436* (2013.01); *A61K 2800/591* (2013.01)

(58) Field of Classification Search
None
See application file for complete search history.

(56) References Cited

U.S. PATENT DOCUMENTS

2007/0213243 A1 * 9/2007 Yao ........................ C11D 9/225
510/130

* cited by examiner

*Primary Examiner* — Brian Gulledge
(74) *Attorney, Agent, or Firm* — Jarrod N. Raphael

(57) ABSTRACT

Disclosed are a liquid pearlescent composition (e.g., a liquid pearlescent concentrate) that is free of a preservative, a personal product including the composition, and a method of use the same.

11 Claims, No Drawings

LIQUID PEARLESCENT COMPOSITION

CROSS-REFERENCE TO RELATED APPLICATION

The present application claims the benefit of priority under 35 U.S.C. § 119(e) of U.S. Provisional Application Ser. No. 62/944,075, filed on Dec. 5, 2019, the entire disclosure of which is incorporated herein by reference.

TECHNICAL FIELD

The present disclosure relates to a liquid pearlescent composition that is self-preserving against both bacterial and fungal contamination, for example, as being used in personal care applications.

BACKGROUND

A commercial personal care product may contain a pearlescent concentrate. Typically, the pearlescent concentrate includes preservatives that are known to be undesirable since some components thereof are corrosive or toxic to skin.

Accordingly, there remains a need for improved pearlescent compositions for use in personal care products.

SUMMARY

The present disclosure relates to a liquid pearlescent composition (e.g., a liquid pearlescent concentration) that is free of a preservative.

In an aspect, provided is a self-preserved pearlizing composition. The composition includes:
a glycol compound having a formula of:

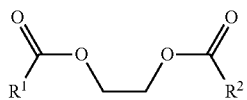

(I)

wherein each $R^1$ and $R^2$ is $C_8$-$C_{20}$ alkyl;
a sulfate compound having a formula of:
$CH_3(CH_2)_{11}(OCH_2CH_2)_nOSO_3X$ (II), wherein n is an integer from 1 to 5, and X is Na or $NH_4$;
an alcohol containing a $C_{12}$-$C_{24}$ alkyl group;
a betaine compound having a formula of:

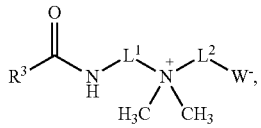

(III)

wherein $R^3$ is $C_8$-$C_{20}$ alkyl, $L^1$ is substituted or unsubstituted $C_1$-$C_5$ alkylene, $L^2$ is substituted or unsubstituted $C_1$-$C_5$ alkylene, W is —COO or —$SO_3$ group;
a salt; and
a solvent.

Particularly, the composition is free of a preservative including a formaldehyde releaser, paraben or a derivative thereof, isothiazolinone or a derivative thereof, a formic acid, or benzoic acid or a derivative thereof.

In embodiments, the composition is free of one or more preservatives selected from formaldehyde, methylchloroisothiazolinone, methylisothiazolinone, benzisothiazolinone, diazoidinyl urea, DMDM hydantoin, sodium hydroxymethylglycinate, ethylparaben, methylparaben, propylparaben, butylparaben, isobutylparaben, phenoxyethanol, benzoic acid, sodium benzoate, caprylyl glycol, and capryhydroxamic acid.

In embodiments, the composition includes one or more additives selected from alkyl ether sulfates; sulfonates; alkyl isethionates; alkyl betaines; alkyl amidopropyl betaines; sulfo-betaines; and alkanolamides.

In embodiments, the composition further includes one or more additives selected from magnesium sulfate, ammonium chloride, glycerine, magnesium carbonate, cetyl alcohol, benzyl alcohol, zinc carbonate, PPG-9, propylene glycol, tetrasodium EDTA, fragrance, natural extracts, citric acid, and sodium hydroxide In embodiments, the sulfate compound includes $CH_3(CH_2)_{11}(OCH_2CH_2)OS_3Na$, $CH_3(CH_2)_{11}(OCH_2CH_2)_2OSO_3Na$, $CH_3(CH_2)_{11}(OCH_2CH_2)_3OSO_3Na$, $CH_3(CH_2)_{11}(OCH_2CH_2)OSO_3NH_4$, $CH_3(CH_2)_{11}(OCH_2CH_2)_2OSO_3NH_4$, or $CH_3(CH_2)_{11}(OCH_2CH_2)_3OSO_3NH_4$.

In embodiments, the glycol compound includes glycol distearate, or glycol monostearate.

In embodiments, the glycol compound includes glycol distearate, or glycol monostearate.

In embodiments, the composition has a pH of about 5.0 to about 7.0.

In embodiments, the salt includes sodium chloride, ammonium chloride or potassium chloride.

In embodiments, the solvent includes water.

In some embodiments, the composition includes: an amount of about 15 to about 25 wt % of the glycol compound; an amount of about 7 to about 15 wt % of the sulfate compound; an amount of about 0.1 to about 1.0 wt % of the alcohol containing a $C_{12}$-$C_{24}$ alkyl group; an amount of about 0.1 to about 1.0 wt % of the betaine compound; an amount of about 0.1 to about 1.0 wt % of the salt; and an amount of about 55 to about 75 wt % of the solvent. All the wt % is based on the total weight of the composition.

In some embodiments, the composition consists of:
the glycol compound having a formula of:

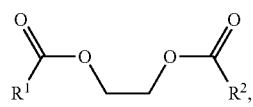

(I)

wherein each $R^1$ and $R^2$ is $C_8$-$C_{20}$ alkyl;
the sulfate compound having a formula of:
$CH_3(CH_2)_{11}(OCH_2CH_2)_nOSO_3X$ (II), wherein n is an integer from 1 to 5 and X is Na or $NH_4$;
the alcohol containing a $C_{12}$-$C_{24}$ alkyl group;
the betaine compound having a formula of

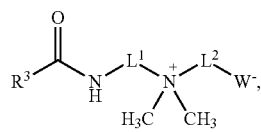

(III)

wherein $R^3$ is $C_8$-$C_{20}$ alkyl, $L^1$ is substituted or unsubstituted $C_1$-$C_5$ alkylene, $L^2$ is substituted or unsubstituted $C_1$-$C_5$ alkylene, and W is —COO or —SO$_3$ group;

the salt; and the solvent.

In embodiments, the composition has a solid content of about 25.0 wt % to about 40.0 wt % based on the total weight of the composition.

In an aspect, provided is a self-preserved pearlizing composition ("composition") including: glycol distearate; sodium laureth sulfate; myristyl alcohol; cocamidopropyl betaine; sodium chloride; and water. Particularly, the composition is free of a preservative comprising a formaldehyde releaser, paraben or a derivative thereof, isothiazolinone or a derivative thereof, a formic acid, or benzoic acid or a derivative thereof.

In embodiments, the composition is free of one or more preservatives selected from formaldehyde, methylchloroisothiazolinone, methylisothiazolinone, benzisothiazolinone, diazoidinyl urea, DMDM hydantoin, sodium hydroxymethylglycinate, ethyl paraben, methyl paraben, propylparaben, butylparaben, isobutylparaben, phenoxyethanol, benzoic acid, sodium benzoate, caprylyl glycol, and capryhydroxamic acid.

In embodiments, the composition further includes one or more additives selected from alkyl ether sulfates; sulfonates; alkyl isethionates; alkyl betaines; alkyl amidopropyl betaines; sulfo betaines; and alkanolamides.

In embodiments, the composition includes: an amount of about 15 to about 25 wt % of the glycol distearate; an amount of about 7 to about 15 wt % of the sodium laureth sulfate; an amount of about 0.1 to about 1.0 wt % of the myristyl alcohol; an amount of about 0.1 to about 1.0 wt % of the cocamidopropyl betaine; an amount of about 0.1 to about 1.0 wt % of the sodium chloride; and an amount of about 55 to about 75 wt % of the water. All the wt % is based on the total weight of the composition.

In embodiments, the composition has a pH of about 5.0 to about 7.0.

In embodiments, the composition has a solid content of about 25.0 wt % to about 40.0 wt % based on the total weight of the composition.

In an aspect, provided is a personal care product including the self-preserved pearlizing composition as described herein.

In an aspect, provided is a method of preventing bacterial and/or fungal contamination in a personal care product. The method includes formulating the personal care product comprising a self-preserved pearlizing composition as described herein.

Other aspects are disclosed infra.

DETAILED DESCRIPTION

Definitions

The terms "pearlescent composition", "pearling composition", "pearlizing composition", "pearlescent agent, or "pearling agent" as used herein refer to an ingredient or a composition added to a personal care product (e.g., hair products, liquid soaps, or body care products) to improve or impart appearance (e.g., shiny look) or texture as well as physical and chemical properties such as stability, density, viscosity, pH, antibacterial properties, or the like.

The terms "self-preserved composition" or self-preserved concentrate" as used herein refer to a composition that can naturally act to preserve its own composition, phase, or properties without addition of preserving components. Particularly, the self-preserved composition can prevent the composition from being contaminated, changed, or decomposed by the existence of bacterial or fungal microorganism that are unintentionally added or occur after formulation or manufacturing. In certain embodiments, the self-preserved composition does not require or include additional chemicals, such as antibiotics, antibacterial agents, or preservatives.

In an embodiment, the terms "free of" and "does not comprise" mean the composition contains no more than an amount of a substance that does not contribute to the composition as an active ingredient (e.g. the substance is not present in an active amount). In an embodiment, the content of the substance is less than an amount of about 100 ppm, less than about 90 ppm, less than about 80 ppm, less than about 70 ppm, less than about 60 ppm, less than about 50 ppm, less than about 40 ppm, less than about 30 ppm, less than about 20 ppm, less than about 10 ppm, less than about 5 ppm, or less than about 1 ppm in a composition. Alternatively, when a composition is free of, or does not comprise or include, a substance, the content thereof is less than about 0.0001 wt %, less than about 0.00009 wt %, less than about 0.00008 wt %, less than about 0.00007 wt %, less than about 0.00006 wt %, less than about 0.00005 wt %, less than about 0.00004 wt %, less than about 0.00003 wt %, less than about 0.00002 wt %, or less than about 0.00001 wt % based on the total weight of the composition. In certain embodiments, when a composition is free of a substance, the composition does not at all include the substance (0 wt %).

The term "preservative" as used herein refers to a substance or a chemical that is added to a product in order to prevent bacterial and/or fungal contamination and the resulting changes. In certain embodiments, the preservative is a naturally-derived, synthetic or artificial substance that is added for preserving purposes. Exemplary preservatives may include formaldehyde releasers, parabens, and isothiazolinones, or derivatives thereof.

The term "glycol compound" as used herein refers to a compound formed by esterification between two hydroxyl (—OH) groups of glycol and one or two fatty acids. In certain embodiments, the fatty acids containing a saturated or unsaturated alkyl group (e.g., 2 to 25 carbon atoms, 5 to 25 carbon atoms, or 8 to 20 carbon atoms) and carboxylate reacted with ethylene glycol to produce the glycol compound.

The term "sulfate compound" as used herein refers to a compound containing a sulfate group (—SO$_4^{2-}$) or a salt thereof. In certain embodiments, the sulfate compound further contains a saturated linear alkyl group (e.g., 8 to 20 carbon atoms). In certain embodiments, the sulfate compound has a structure of $CH_3(CH_2)_{11}(OCH_2CH_2)_n OSO_3Na$ or $CH_3(CH_2)_{11}(OCH_2CH_2)_n OSO_3NH_4$ (n=1 to 5).

The term "alcohol compound" as used herein refers to a compound containing at least one hydroxyl (—OH) group. In certain embodiments, the alcohol compound contains alkyl group (e.g., 2 to 25 carbon atoms, 5 to 25 carbon atoms, 10 to 25 carbon atoms or 12 to 24 carbon atoms) where the hydroxy group is attached.

The term "betaine compound" as used herein refers to a compound containing both one or more cationic functional group (e.g., quaternary ammonium or phosphonium cation) and one or more anionic functional groups (e.g., carboxylate) such that the compound is neutral as a whole. In certain embodiments, the betaine compound is a zwitterion including a quaternary ammonium and a carboxylate group.

The term "formaldehyde releaser" as used herein refers to a substance or compound that releases formaldehyde (e.g., H—CHO).

The term "paraben

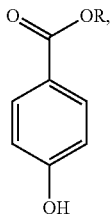

and derivative thereof" as used herein refers to a compound having a core structure of paraben, and derivatives, for example, having various substituents at R position and other atoms (e.g., carbon or oxygen), or a salt form thereof.

The term "isothiazolinone or a derivative thereof" as used herein refers to a compound having a core structure of

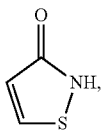

and its derivatives, for example, having various substituents at carbon, nitrogen, or sulfur atoms, or a salt form thereof.

The term "benzoic acid or a derivative thereof" as used herein refers to a compound having a core structure of benzoic acid,

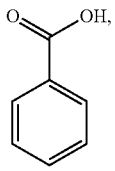

and derivatives (e.g., salt). The compound may exist as a salt form, e.g.,

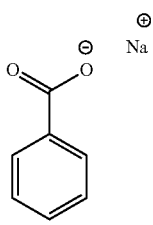

In addition, the derivative thereof may have various substituents on the phenyl ring.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "weight %" or "wt %" of a component as used herein is a relative amount to the total weight of the composition.

The term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Compositions

Provided herein, inter alia, are compositions, or self-preserved pearlizing compositions, that are free of preservatives (e.g., a formaldehyde releaser, paraben or a derivative thereof, isothiazolinone or a derivative thereof, a formic acid, or benzoic acid or a derivative thereof).

In embodiments, the compositions are free of one or more preservatives selected from formaldehyde, methylchloroisothiazolinone, methylisothiazolinone, benzisothiazolinone, diazoidinyl urea, DMDM hydantoin, sodium hydroxymethylglycinate, ethyl paraben, methyl paraben, propylparaben, butylparaben, isobutylparaben, phenoxyethanol, benzoic acid, sodium benzoate, caprylyl glycol, and capryhydroxamic acid.

In an aspect, provided is a self-preserved pearlizing composition. In an embodiment, the composition includes: a glycol compound, a sulfate compound, an alcohol, a betaine compound, a salt, and a solvent.

The glycol compound may have a formula of:

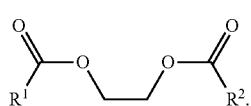

(I)

Each $R^1$ and $R^2$ is $C_8$-$C_{20}$ alkyl.

In embodiments, $R^1$ and $R^2$ are the same alkyl group. In embodiments, $R^1$ and $R^2$ are different alkyl groups. In embodiments, $R^1$ is unsubstituted saturated $C_8$ alkyl. In embodiments, $R^1$ is unsubstituted unsaturated $C_8$ alkyl. In embodiments, $R^1$ is unsubstituted saturated $C_9$ alkyl. In embodiments, $R^1$ is unsubstituted unsaturated $C_9$ alkyl. In embodiments, $R^1$ is unsubstituted saturated $C_{10}$ alkyl. In embodiments, $R^1$ is unsubstituted unsaturated $C_{10}$ alkyl. In embodiments, $R^1$ is unsubstituted saturated $C_{11}$ alkyl. In embodiments, $R^1$ is unsubstituted unsaturated $C_{11}$ alkyl. In embodiments, $R^1$ is unsubstituted saturated $C_{12}$ alkyl. In embodiments, $R^1$ is unsubstituted unsaturated $C_{12}$ alkyl. In embodiments, $R^1$ is unsubstituted saturated $C_{13}$ alkyl. In embodiments, $R^1$ is unsubstituted unsaturated $C_{13}$ alkyl. In embodiments, $R^1$ is unsubstituted saturated $C_{14}$ alkyl. In embodiments, $R^1$ is unsubstituted unsaturated $C_{14}$ alkyl. In embodiments, $R^1$ is unsubstituted saturated $C_{15}$ alkyl. In embodiments, $R^1$ is unsubstituted unsaturated $C_{15}$ alkyl. In embodiments, $R^1$ is unsubstituted saturated $C_{16}$ alkyl. In embodiments, $R^1$ is unsubstituted unsaturated $C_{16}$ alkyl. In embodiments, $R^1$ is unsubstituted saturated $C_{17}$ alkyl. In embodiments, $R^1$ is unsubstituted unsaturated $C_{17}$ alkyl. In embodiments, $R^1$ is unsubstituted saturated $C_{18}$ alkyl. In embodiments, $R^1$ is unsubstituted unsaturated $C_{15}$ alkyl. In embodiments, $R^1$ is unsubstituted saturated $C_{19}$ alkyl. In embodiments, $R^1$ is unsubstituted unsaturated $C_{19}$ alkyl. In embodiments, $R^1$ is unsubstituted saturated $C_{20}$ alkyl. In embodiments, $R^1$ is unsubstituted unsaturated $C_{20}$ alkyl.

In embodiments, $R^2$ is unsubstituted saturated $C_8$ alkyl. In embodiments, $R^2$ is unsubstituted unsaturated $C_8$ alkyl. In embodiments, $R^2$ is unsubstituted saturated $C_9$ alkyl. In embodiments, $R^2$ is unsubstituted unsaturated $C_9$ alkyl. In embodiments, $R^2$ is unsubstituted saturated $C_{10}$ alkyl. In embodiments, $R^2$ is unsubstituted unsaturated $C_{10}$ alkyl. In embodiments, $R^2$ is unsubstituted saturated $C_{11}$ alkyl. In embodiments, $R^2$ is unsubstituted unsaturated $C_{11}$ alkyl. In embodiments, $R^2$ is unsubstituted saturated $C_{12}$ alkyl. In embodiments, $R^2$ is unsubstituted unsaturated $C_{12}$ alkyl. In embodiments, $R^2$ is unsubstituted saturated $C_{13}$ alkyl. In embodiments, $R^2$ is unsubstituted unsaturated $C_{13}$ alkyl. In embodiments, $R^2$ is unsubstituted saturated $C_{14}$ alkyl. In embodiments, $R^2$ is unsubstituted unsaturated $C_{14}$ alkyl. In embodiments, $R^2$ is unsubstituted saturated $C_{15}$ alkyl. In embodiments, $R^2$ is unsubstituted unsaturated $C_{15}$ alkyl. In embodiments, $R^2$ is unsubstituted saturated $C_{16}$ alkyl. In embodiments, $R^2$ is unsubstituted unsaturated $C_{16}$ alkyl. In embodiments, $R^2$ is unsubstituted saturated $C_{17}$ alkyl. In embodiments, $R^2$ is unsubstituted unsaturated $C_{17}$ alkyl. In embodiments, $R^2$ is unsubstituted saturated $C_{18}$ alkyl. In embodiments, $R^2$ is unsubstituted unsaturated $C_{15}$ alkyl. In embodiments, $R^2$ is unsubstituted saturated $C_{19}$ alkyl. In embodiments, $R^2$ is unsubstituted unsaturated $C_{19}$ alkyl. In embodiments, $R^2$ is unsubstituted saturated $C_{20}$ alkyl. In embodiments, $R^2$ is unsubstituted unsaturated $C_{20}$ alkyl.

In embodiments, the glycol compound includes glycol distearate or glycol monostearate. In embodiments, the glycol compound is glycol distearate. In embodiments, the glycol compound is glycol monostearate.

In embodiments, the sulfate compound has a formula of $CH_3(CH_2)_{11}(OCH_2CH_2)_nOSO_3X$ (II) where n is an integer from 1 to 5 and X is Na or $NH_4$.

In embodiments, n is 1. In embodiments, n is 2. In embodiments, n is 3. In embodiments, n is 4. In embodiments, n is 5. In embodiments, the sulfate compound includes $CH_3(CH_2)_{11}(OCH_2CH_2)OS_3Na$, $CH_3(CH_2)_{11}(OCH_2CH_2)_2OSO_3Na$, $CH_3(CH_2)_{11}(OCH_2CH_2)_3OSO_3Na$, $CH_3(CH_2)_{11}(OCH_2CH_2)OS_3NH_4$, $CH_3(CH_2)_{11}(OCH_2CH_2)_2 OSO_3NH_4$, or $CH_3(CH_2)_{11}(OCH_2CH_2)_3 OSO_3NH_4$. In embodiments, the sulfate compound includes $CH_3(CH_2)_{11}(OCH_2CH_2)OS_3Na$. In embodiments, the sulfate compound includes $CH_3(CH_2)_{11}(OCH_2CH_2)_2OSO_3Na$. In embodiments, the sulfate compound includes $CH_3(CH_2)_{11}(OCH_2CH_2)_3OSO_3Na$. In embodiments, the sulfate compound includes $CH_3(CH_2)_{11}(OCH_2CH_2)OS_3NH_4$. In embodiments, the sulfate compound includes $CH_3(CH_2)_{11}(OCH_2CH_2)_2OSO_3NH_4$. In embodiments, the sulfate compound includes $CH_3(CH_2)_{11}(OCH_2CH_2)_3OSO_3NH_4$.

In embodiments, the alcohol compound contains a $C_{12}$-$C_{24}$ alkyl group. In embodiments, the alcohol compound contains a $C_{12}$-$C_{24}$ linear alkyl group. In embodiments, the alcohol compound contains a $C_{12}$ linear alkyl group. In embodiments, the alcohol compound contains a $C_{13}$ linear alkyl group. In embodiments, the alcohol compound contains a $C_{14}$ linear alkyl group. In embodiments, the alcohol compound contains a $C_{15}$ linear alkyl group. In embodiments, the alcohol compound contains a $C_{16}$ linear alkyl group. In embodiments, the alcohol compound contains a $C_{17}$ linear alkyl group. In embodiments, the alcohol compound contains a $C_{15}$ linear alkyl group. In embodiments, the alcohol compound contains a $C_{19}$ linear alkyl group. In embodiments, the alcohol compound contains a $C_{20}$ linear alkyl group. In embodiments, the alcohol compound contains a $C_{21}$ linear alkyl group. In embodiments, the alcohol compound contains a $C_{22}$ linear alkyl group. In embodiments, the alcohol compound contains a $C_{23}$ linear alkyl group. In embodiments, the alcohol compound contains a $C_{24}$ linear alkyl group. In embodiments, the alcohol compound contains a $C_{12}$-$C_{24}$ branched alkyl group. In embodiments, the alcohol compound contains a $C_{12}$ branched alkyl group. In embodiments, the alcohol compound contains a $C_{13}$ branched alkyl group. In embodiments, the alcohol compound contains a $C_{14}$ branched alkyl group. In embodiments, the alcohol compound contains a $C_{15}$ branched alkyl group. In embodiments, the alcohol compound contains a $C_{16}$ branched alkyl group. In embodiments, the alcohol compound contains a $C_{17}$ branched alkyl group. In embodiments, the alcohol compound contains a $C_{15}$ branched alkyl group. In embodiments, the alcohol compound contains a $C_{19}$ branched alkyl group. In embodiments, the alcohol compound contains a $C_{20}$ branched alkyl group. In embodiments, the alcohol compound contains a $C_{21}$ branched alkyl group. In embodiments, the alcohol compound contains a $C_{22}$ branched alkyl group. In embodiments, the alcohol compound contains a $C_{23}$ branched alkyl group. In embodiments, the alcohol compound contains a $C_{24}$ branched alkyl group. In embodiments, the alcohol compound is myristyl alcohol (1-tetradecanol, or $C_{14}H_{30}O$).

The betaine compound has a formula of

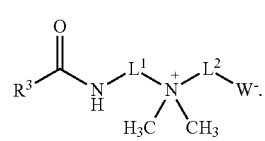

(III)

$R^3$ is $C_8$-$C_{20}$ alkyl. $L^1$ is substituted or unsubstituted $C_1$-$C_5$ alkylene and $L^2$ is substituted or unsubstituted $C_1$-$C_5$ alkylene. W is —COO or —$SO_3$ group.

In embodiments, W is carboxyl group (—COO). In embodiments, W is sulfate group (—$SO_3$).

In embodiments, $R^3$ is unsubstituted saturated $C_8$ alkyl. In embodiments, $R^3$ is unsubstituted unsaturated $C_8$ alkyl. In embodiments, $R^3$ is unsubstituted saturated $C_9$ alkyl. In embodiments, $R^3$ is unsubstituted unsaturated $C_9$ alkyl. In embodiments, $R^3$ is unsubstituted saturated $C_{10}$ alkyl. In embodiments, $R^3$ is unsubstituted unsaturated $C_{10}$ alkyl. In embodiments, $R^3$ is unsubstituted saturated $C_{11}$ alkyl. In embodiments, $R^3$ is unsubstituted unsaturated $C_{11}$ alkyl. In embodiments, $R^3$ is unsubstituted saturated $C_{12}$ alkyl. In embodiments, $R^3$ is unsubstituted unsaturated $C_{12}$ alkyl. In embodiments, $R^3$ is unsubstituted saturated $C_{13}$ alkyl. In embodiments, $R^3$ is unsubstituted unsaturated $C_{13}$ alkyl. In embodiments, $R^3$ is unsubstituted saturated $C_{14}$ alkyl. In embodiments, $R^3$ is unsubstituted unsaturated $C_{14}$ alkyl. In embodiments, $R^3$ is unsubstituted saturated $C_{15}$ alkyl. In embodiments, $R^3$ is unsubstituted unsaturated $C_{15}$ alkyl. In embodiments, $R^3$ is unsubstituted saturated $C_{16}$ alkyl. In embodiments, $R^3$ is unsubstituted unsaturated $C_{16}$ alkyl. In embodiments, $R^3$ is unsubstituted saturated $C_{17}$ alkyl. In embodiments, $R^3$ is unsubstituted unsaturated $C_{17}$ alkyl. In embodiments, $R^3$ is unsubstituted saturated $C_{18}$ alkyl. In embodiments, $R^3$ is unsubstituted unsaturated $C_{15}$ alkyl. In embodiments, $R^3$ is unsubstituted saturated $C_{19}$ alkyl. In embodiments, $R^3$ is unsubstituted unsaturated $C_{19}$ alkyl. In embodiments, $R^3$ is unsubstituted saturated $C_{20}$ alkyl. In embodiments, $R^3$ is unsubstituted unsaturated $C_{20}$ alkyl.

In embodiments, $L^1$ is substituted or unsubstituted $C_1$-$C_5$ alkylene. In embodiments, $L^1$ is substituted $C_1$-$C_5$ alkylene. In embodiments, $L^1$ is OH-substituted $C_1$-$C_5$ alkylene. In embodiments, $L^1$ is unsubstituted $C_1$-$C_5$ alkylene. In embodiments, $L^1$ is substituted $C_3$ alkylene. In embodiments, $L^1$ is OH-substituted $C_3$ alkylene. In embodiments, $L^1$ is unsubstituted $C_3$ alkylene.

In embodiments, $L^2$ is substituted or unsubstituted $C_1$-$C_5$ alkylene. In embodiments, $L^2$ is substituted $C_1$-$C_5$ alkylene. In embodiments, $L^2$ is OH-substituted $C_1$-$C_5$ alkylene. In embodiments, $L^2$ is unsubstituted $C_1$-$C_5$ alkylene. In embodiments, $L^2$ is substituted $C_3$ alkylene. In embodiments, $L^2$ is OH-substituted $C_3$ alkylene. In embodiments, $L^2$ is unsubstituted $C_3$ alkylene.

In embodiments, the betaine compound includes, but not limited to, cocamidopropyl betaine, lauramidopropyl betaine, lauryl betaine, coco betaine, cocamidopropyl hydroxysultaine, lauramidopropyl hydroxysultaine, or lauryl hydroxysultaine. In embodiments, the betaine compound includes a cocamidopropyl betaine. In embodiments, the betaine compound is a lauramidopropyl betaine. In embodiments, the betaine compound is a lauryl betaine. In embodiments, the betaine compound is a coco betaine. In embodiments, the betaine compound is a cocamidopropyl hydroxysultaine. In embodiments, the betaine compound is a lauramidopropyl hydroxysultaine. In embodiments, the betaine compound is a lauryl hydroxysultaine. In embodiments, the betaine compound includes cocamidopropyl betaine and one or more compounds selected from the group consisting of lauramidopropyl betaine, lauryl betaine, coco betaine, cocamidopropyl hydroxysultaine, lauramidopropyl hydroxysultaine, and lauryl hydroxysultaine.

In embodiments, the composition has a pH of about 5.0 to about 7.0. In embodiments, the composition has a pH of about 5.2. In embodiments, the composition has a pH of about 5.4. In embodiments, the composition has a pH of about 5.6. In embodiments, the composition has a pH of about 5.8. In embodiments, the composition has a pH of about 6.0. In embodiments, the composition has a pH of about 6.2. In embodiments, the composition has a pH of about 6.4. In embodiments, the composition has a pH of about 6.6. In embodiments, the composition has a pH of about 6.8. In embodiments, the composition has a pH of about 7.0. In embodiments, the composition may be suitably adjusted using techniques.

In embodiments, the salt suitably may include any salts that may be used in a personal care product. For example, salts in the composition do not cause any irritation to a body (e.g., skin, scalp, or hair), induce any changes (e.g., chemical changes, chemical reaction or change pH) or reaction among the components thereof. Exemplary salts may include, but is not limited to, sodium chloride, ammonium chloride or potassium chloride.

In embodiments, the solvent of the composition includes water. In embodiments, the solvent may further include organic solvent that is miscible to water. In embodiments, the solvent may further include organic solvent that is not miscible to water.

In embodiments, the composition further includes one or more additives. The additives may include surfactants (e.g., anionic, amphoteric, cationic, or non-ionic surfactant). Exemplary anionic surfactant may include, but not be limited to, alkyl sulfates (e.g., ammonium lauryl sulfate, sodium lauryl sulfate, sodium coco sulfate, ammonium coco sulfate, triethanolamine lauryl sulfate, and the like), alkyl ether sulfates (e.g., ammonium laureth sulfate, sodium laureth sulfate, or sodium trideceth sulfate, and the like), sulfonates (e.g., sodium olefin sulfonate. TEA-dodecylbenzene sulfonate, sodium xylene sulfonate, and the like), sulfosuccinates (e.g., disodium lauryl sulfosuccinate, disodium laureth sulfosuccinate, disodium peg-12 dimethicone sulfosuccinate, disodium cocamido MIPA sulfosuccinate, disodium oleamido MIPA sulfosuccinate, disodium ricinoaleamido MEA sulfosuccinate, and the like), alkyl taurates (e.g., sodium methyl cocoyl taurate, sodium methyl oleyl taurate, and the like), alkyl phosphates (e.g., laureth-1 phosphate, laureth-3 phosphate, potassium laureth-1 phosphate, sodium laureth-1 phosphate, and the like), carboxylates (e.g., sodium laureth-13 carboxylate, sodium 12-15 pareth-12 carboxylate, sodium 12-13 pareth-8 carboxylate, trideceth-7 carboxylic acid, and the like), alkyl glycinates (e.g., sodium lauroyl glycinate, sodium cocoyl glycinate, and the like), alkyl isethionates (e.g., sodium cocoyl isethionate, sodium lauroyl isethionate, sodium lauroyl methyl isethionate, and the like), alkyl sarcosinate (e.g., sodium lauroyl sarcosinate, and the like).

Exemplary amphoteric surfactants may include, but not be limited to, other bataines (e.g., babassuamidopropyl betaine, oleamidopropyl betaine, and the like), amphoacetates (e.g., disodium cocamidodiacetate, sodium cocoamphoacetate, disodium lauroamphodiacetate, sodium lauroamphoacetate, and the like), or amphopropionates (e.g., disodium cocoamphodipropionate and the like). Exemplary non-Ionic Surfactants may include, but not limited to, alkanolamides (e.g., cocamide MEA, lauramide MEA, stearamide MEA, cocamide MIPA, lauramide MIPA, cocamide DEA, lauramide DEA, soyamide DEA, and the like), or poly Sorbates (e.g., polysorbate 20, PEG-80 sorbitan 1 aurate, and the like). Exemplary cationic surfactants may include, but not be limited to, isostearamidopropyl ethyldimonium ethosulfate (and) PEG-9, amidopropyl ethyldimonium ethosulfate, PEG-9, isostearamidopropyl morpholine lactate, cetrimonium chloride, stearalkonium chloride, behentrimonium chloride, and the like.

The additives may include conditioning proteins, for example, cocodimonium hydroxypropyl hydrolyzed silk protein, cocodimonium hydroxypropyl hydrolyzed rice protein, cocodimonium hydroxypropyl hydrolyzed wheat protein, quaternium-79 hydrolyzed keratin protein, wheat germami-dipropyldimonium hydrosypropyl hydrolyzed wheat protein, wheat germamidopropyl dimethylamine hydrolyzed wheat protein.

The additives may include synthetic conditioning agents, for example, polyquaternium-2, polyquaternium-6, polyquaternuim-7, polyquaternium-10, polymethylacrylamidopropyltrimonium chloride, and the like. The additives may include natural based conditioning agents, for example, (Guar) hydroxypropyl trimonium chloride, hydroxypropyl (Guar) hydroxypropyltrimonium chloride, and the like.

The additives may include natural rheology modifiers, for example, xanthan gum, hydropropyl guar, cyamosis tetragonolba (Guar) gum, succinoglycan, and the like.

In embodiments, the additives may include, but not be limited to, magnesium sulfate, ammonium chloride, glycerine, magnesium carbonate, cetyl alcohol, benzyl alcohol, zinc carbonate, PPG-9, propylene glycol, tetrasodium EDTA, fragrance, natural extracts, citric acid, and sodium hydroxide.

In an exemplary embodiment, the composition includes: an amount of about 15 to about 25 wt % of the glycol compound; an amount of about 7 to about 15 wt % of the sulfate compound; an amount of about 0.1 to about 1.0 wt % of the alcohol containing a $C_{12}$-$C_{24}$ alkyl group; an amount of about 0.1 to about 1.0 wt % of the betaine compound; an amount of about 0.1 to about 1.0 wt % of the salt; and an amount of about 55 to about 75 wt % of the solvent. All the wt % is based on the total weight of the composition.

In embodiments, the composition may consist essentially of, essentially consist of, or consistent of the components described above. In an exemplary embodiments, the composition may consist essentially of, essentially consist of, or consistent of: the glycol compound, the sulfate compound, the alcohol, the betaine compound, the salt, and the solvent. In an exemplary embodiments, the composition may consist of the glycol compound, the sulfate compound, the alcohol, the betaine compound, the salt, and the solvent.

In embodiments, the composition has a solid content of about 25.0 wt % to about 40.0 wt % based on the total weight of the composition. In embodiments, the composition has a solid content of about 30.0 wt % to about 40.0 wt % based on the total weight of the composition. In embodiments, the composition has a solid content of about 25.0 wt % to about 35.0 wt % based on the total weight of the composition. In embodiments, the composition has a solid content of about 25.0 wt % to about 30.0 wt % based on the total weight of the composition.

In an aspect, the composition includes glycol distearate, sodium laureth sulfate, myristyl alcohol, cocamidopropyl betaine, sodium chloride; and water. Particularly, the composition is free of a preservative that may include a formaldehyde releaser, paraben or a derivative thereof, isothiazolinone or a derivative thereof, a formic acid, or benzoic acid. For example, the composition is free of one or more preservatives selected from formaldehyde, methylchloroisothiazolinone, methylisothiazolinone, benzisothiazolinone, diazoidinyl urea, DMDM hydantoin, sodium hydroxymethlyglycinate, ethyl paraben, methyl paraben, propylparaben, butylparaben, isobutylparaben, phenoxyethanol, benzoic acid, sodium benzoate, caprylyl glycol, and capryhydroxamic acid. In embodiments, the composition may include one or more additives selected from alkyl ether sulfates; sulfonates; alkyl isethionates; alkyl betaines; alkyl amidopropyl betaines; sulfo betaines; and alkanolamides.

In an exemplary embodiments, the composition includes an amount of about 15 to about 25 wt % of the glycol distearate; an amount of about 7 to about 15 wt % of the sodium laureth sulfate; an amount of about 0.1 to about 1.0 wt % of the myristyl alcohol; an amount of about 0.1 to about 1.0 wt % of the cocamidopropyl betaine; an amount of about 0.1 to about 1.0 wt % of the sodium chloride; and an amount of about 55 to about 75 wt % of the water. All the wt % is based on the total weight of the composition.

Products and Methods

In an aspect, provided is a personal care product that includes the self-preserved pearlizing composition, or composition, as described herein. In embodiments, the composition includes a glycol compound, a sulfate compound, an alcohol, a betaine compound, a salt, and a solvent. For example, the composition includes glycol distearate, sodium laureth sulfate, myristyl alcohol, cocamidopropyl betaine, sodium chloride; and water.

In embodiments, the product is free of a preservative that may include a formaldehyde releaser, paraben or a derivative thereof, isothiazolinone or a derivative thereof, a formic acid or derivative thereof, or benzoic acid or a derivative thereof. For example, the product is free of one or more preservatives selected from the group consisting of formaldehyde, methylchloroisothiazolinone, methylisothiazolinone, benzisothiazolinone, diazoidinyl urea, DMDM hydantoin, sodium hydroxymethlyglycinate, ethyl paraben, methyl paraben, propylparaben, butylparaben, isobutylparaben, phenoxyethanol, benzoic acid, sodium benzoate, caprylyl glycol, and capryhydroxamic acid. In embodiments, the product does not include an antibacterial agent.

In an aspect, provided is a method of preventing bacterial and/or fungal contamination in a personal care product. The method includes: formulating the personal care product including the self-preserved pearlizing composition, or the composition as described herein.

EXAMPLE

Some specific exemplary embodiments are described in the detail below.

Example: Compositions

Exemplary compositions of pearlizing agents are described in Table 1.

TABLE 1

| CAS# | INCI Name | wt % |
|---|---|---|
| Composition 1 | | |
| 7732-18-5 | Water | 69.3 |
| 627-83-6 | Glycol Distearate | 19 |
| 68585-34-2 | Sodium Laureth Sulfate | 10 |
| 112-72-1 | myristyl alcohol | 0.5 |
| 70851-07-9 | Cocamidopropyl Betaine | 0.5 |
| 7647-14-5 | Sodium Chloride | 0.5 |
| 532-32-1 | Sodium Benzoate | 0.1 |
| 2682-20-4 | Methylisothiazolinone | 0.095 |
| Specifications | | |
| pH (10% aq) | 4.0-5.0 | |
| Total Solids % | 29.0-35.0 | |
| Composition 2 | | |
| 7732-18-5 | Water | 69.3 |
| 627-83-6 | Glycol Distearate | 19 |
| 68585-34-2 | Sodium Laureth Sulfate | 10 |
| 112-72-1 | myristyl alcohol | 0.5 |
| 70851-07-9 | Cocamidopropyl Betaine | 0.5 |
| 7647-14-5 | Sodium Chloride | 0.5 |

TABLE 1-continued

| CAS# | INCI Name | wt % |
|---|---|---|
| 532-32-1 | Sodium Benzoate | 0.1 |
| 2682-20-4 | Methylisothiazolinone | 0.095 |
| Specifications | | |
| pH (10% aq) | 4.0-5.0 | |
| Total Solids % | 29.0-35.0 | |
| | Composition 3 | |
| 7732-18-5 | Water | 69.5 |
| 627-83-6 | Glycol Distearate | 19 |
| 68585-34-2 | Sodium Laureth Sulfate | 10 |
| 112-72-1 | Myristoyl Alcohol | 0.5 |
| 70851-07-9 | Cocamidopropyl Betaine | 0.5 |
| 7647-14-5 | Sodium Chloride | 0.5 |
| Specifications | | |
| pH (10% aq) | 5.0-7.0 | |
| Total Solids % | 29.0-35.0 | |

Test Example 1

Composition 2 above was treated with benzisothiazolinone (BIT) or unpreserved, and aged for four weeks at 40° C. and then sent for microbial challenge testing.

| Example 1 | - Unpreserved - | Aged for 4 weeks at 40° C. |
|---|---|---|
| Example 2 | - 200 ppm BIT | Aged for 4 weeks at 40° C. |

Procedure: Based on ASTM D2574
In-Container Preservative Effectiveness Testing & USP <51> Antimicrobial Preservative Effectiveness The *U.S. Pharmacopeia XXI* <51> states effective preservation of the product if the following conditions are met: "(a) the concentrations of viable bacteria are reduced to not more than 0.1% of the initial concentrations by the $14^{th}$ day; (b) the concentrations of viable yeasts and molds remain at or below the initial concentrations during the first 14 days.

In order to prove the absence of microbiological contamination in the original samples, negative controls were run at the beginning, middle, and end of the experiment to show that any growth observed occurred as a result of the inoculation. Two separate challenges were performed: ATCC Bacterial Pool, ATCC Fungal Pool. The single-inoculation 28 day protocol of USP <51> was enhanced with the addition of a second inoculation on Day 7 as seen in ASTM D2574 (*In-Container Preservative Effectiveness Testing*).

| Bacterial Inoculum Pool: | *Pseudomonas aeruginosa* | ATCC 9027 |
|---|---|---|
| | *Escherichia coli* | ATCC 8739 |
| | *Staphylococcus aureus* | ATCC 6538 |
| Fungal Inoculum Pool: | *Candida albicans* (Yeast) | ATCC 10231 |
| | *Aspergillus brasiliensis* (Mold) | ATCC 16404 |

The standard Bacterial and Fungal inoculum pools were prepared at strengths of $10^8$ CFU/mL and inoculated at strengths of $10^6$ CFU/mL into separate vials of the samples on Day 0 (the beginning of Inoculation I) and then prepared anew and reinoculated into the same vials on Day 7 (the beginning of Inoculation II).

After inoculation sample vials were incubated at 25° C. The samples were run in triplicate. Bacterial recovery was determined by plating 100 μL of the sample onto Tryptic Soy Agar and using the following ratings system in Table 3 to assign the appropriate score. Fungal recovery was determined by the same method and was plated onto Potato Dextrose Agar.

Results and Discussion:

Based on the following results seen in Table 2 below, all provided samples of composition 2, either preserved with 200 ppm of active benzisothiazolinone or unpreserved, effectively controlled against both bacterial and fungal contamination in accordance with the criteria described above (*U.S. Pharmacopeia XXI* <51>).

TABLE 2

Bacterial and Fungal Challenges in Example 2

| | | Inoculation I | | | Inoculation II | | |
|---|---|---|---|---|---|---|---|
| Preservative | Aged | Day 0 | Day 1 | Day 7 | Day 7 | Day 8 | Day 14 |
| BACTERIAL CHALLENGE | | | | | | | |
| None | 40° C. | 4, 4, 4 | 2, 2, 2 | 0, 0, 0 | 4, 4, 4 | 0, 1, 1 | 0, 0, 0 |
| 200 ppm BIT | 40° C. | 4, 4, 4 | 0, 0, 0 | 0, 0, 0 | 4, 4, 4 | 0, 0, 0 | 0, 0, 0 |
| FUNGAL CHALLENGE | | | | | | | |
| None | 40° C. | 3, 3, 3 | 0, 0, 0 | 0, 0, 0 | 2, 2, 2 | 0, 0, 0 | 0, 0, 0 |
| 200 ppm BIT | 40° C. | 3, 3, 3 | 0, 0, 0 | 0, 0, 0 | 2, 2, 2 | 0, 0, 0 | 0, 0, 0 |

*The only bacterial recovery on Day 1 of both inoculations was the Gram-Negative bacteria *Escherichia coli* and *Pseudomonas aeruginosa*.

TABLE 3

Ratings System

| Colonies on Plate | CFU/mL | Score |
|---|---|---|
| None | <10 | 0 |
| 1-9 | <100 | 1 |
| 10-99 | <1000 | 2 |
| >100 distinct colonies | >1000 | 3 |
| TNTC (too numerous to count) | TNTC | 4 |

Test Example 2

Composition 3 above was treated with Lincoserve™ FG-50 (a food-grade preservative blend of potassium sorbate and sodium benzoate) or unpreserved, and aged for four weeks at 45° C. and then sent for microbial challenge testing.

Sample Description:

| | |
|---|---|
| Example 3 - Unpreserved - | Aged for 4 weeks at 45° C. |
| Example 4 - 200 ppm 0.6% Lincoserve ™ FG-50 | Aged for 4 weeks at 45° C. |

Procedure: Based on: ASTM D2574
In-Container Preservative Effectiveness Testing & USP <51> Antimicrobial Preservative Effectiveness In order to prove the absence of microbiological contamination in the original samples, negative controls were run at the beginning, middle, and end of the experiment to show that any growth observed occurred as a result of the inoculation. Two separate challenges were performed: ATCC Bacterial Pool, ATCC Fungal Pool. The single-inoculation 28 day protocol of USP <51> was enhanced with the addition of a second inoculation on Day 7 as seen in ASTM D2574 (*In-Container Preservative Effectiveness Testing*).

| | | |
|---|---|---|
| Bacterial Inoculum Pool: | *Pseudomonas aeruginosa* | ATCC 9027 |
| | *Escherichia coli* | ATCC 8739 |
| | *Staphylococcus aureus* | ATCC 6538 |
| Fungal Inoculum Pool: | *Candida albicans* (Yeast) | ATCC 10231 |
| | *Aspergillus brasiliensis* (Mold) | ATCC 16404 |

The standard Bacterial and Fungal inoculum pools were prepared at strengths of $10^8$ CFU/mL and inoculated at strengths of $10^6$ CFU/mL into separate vials of the samples on Day 0 (the beginning of Inoculation I) and then prepared anew and reinoculated into the same vials on Day 7 (the beginning of Inoculation II).

After inoculation sample vials were incubated at 25° C. The samples were run in triplicate. Bacterial recovery was determined by plating 100 μL of the sample onto Tryptic Soy Agar and using the following ratings system in Table 3 to assign the appropriate score. Fungal recovery was determined by the same method and was plated onto Potato Dextrose Agar.

Results and Discussion:

Based on the following results seen in Table 4 all provided samples of composition 3, both the unpreserved sample and the one containing 0.6% Lincoserve FG-50, effectively controlled against both bacterial and fungal contamination in accordance with the criteria described above.

TABLE 4

Bacterial and Fungal Challenges in TEST EXAMPLE 2

| | | Inoculation I | | | Inoculation II | | |
|---|---|---|---|---|---|---|---|
| Preservative | Aged | Day 0 | Day 1 | Day 7 | Day 7 | Day 8 | Day 14 |
| | | BACTERIAL CHALLENGE | | | | | |
| None | 45° C. | 4, 4, 4 | 0, 0, 0 | 0, 0, 0 | 4, 4, 4 | 1, 0, 0 | 0, 0, 0 |
| Lincoserve FG-50 | 45° C. | 4, 4, 4 | 0, 0, 0 | 0, 0, 0 | 4, 4, 4 | 0, 0, 0 | 0, 0, 0 |
| | | FUNGAL CHALLENGE | | | | | |
| None | 45° C. | 3, 3, 3 | 1, 1, 0 | 0, 0, 0 | 2, 2, 2 | 0, 0, 0 | 0, 0, 0 |
| Lincoserve FG-50 | 45° C. | 3, 3, 3 | 0, 1, 0 | 0, 0, 0 | 2, 2, 2 | 0, 0, 0 | 0, 0, 0 |

The rating system of Table 1 above was used for this evaluation.

The disclosed subject matter has been described with reference to specific details of particular embodiments thereof. It is not intended that such details be regarded as limitations upon the scope of the disclosed subject matter except insofar as and to the extent that they are included in the accompanying claims. Therefore, the exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the exemplary embodiments described herein. The exemplary embodiments described herein illustratively disclosed herein suitably may be practiced in the absence of any element that is not specifically disclosed herein and/or any optional element disclosed herein.

What we claim:

1. A self-preserved pearlizing composition consisting of: a glycol compound having a formula of:

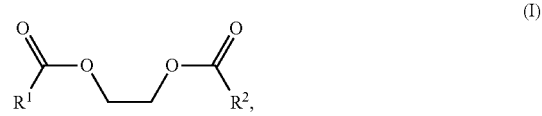

(I)

wherein each $R^1$ and $R^2$ is $C_8$-$C_{20}$ alkyl;
a sulfate compound having a formula of:
$CH_3(CH_2)_{11}(OCH_2CH_2)_nOSO_3X$ (II), wherein n is an integer from 1 to 5 and X is Na or $NH_4$;
an alcohol containing a $C_{12}$-$C_{24}$ alkyl group;
a betaine compound having a formula of:

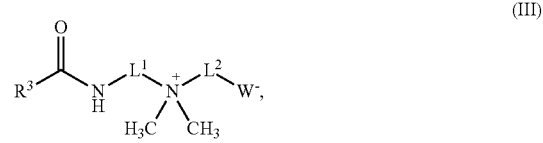

(III)

wherein $R^3$ is $C_8$-$C_{20}$ alkyl; $L^1$ is substituted or unsubstituted $C_1$-$C_5$ alkylene; $L^2$ is substituted or unsubstituted $C_1$-$C_5$ alkylene; and W is —COO or —$SO_3$ group;
a salt; and
a solvent.

2. The self-preserved pearlizing composition of claim 1, wherein the sulfate compound comprises $CH_3(CH_2)_{11}(OCH_2CH_2)OSO_3Na$, $CH_3(CH_2)_{11}(OCH_2CH_2)_2OSO_3Na$, $CH_3(CH_2)_{11}(OCH_2CH_2)_3OSO_3Na$, $CH_3(CH_2)_{11}(OCH_2CH_2)OSO_3NH_4$, $CH_3(CH_2)_{11}(OCH_2CH_2)_2OSO_3NH_4$, or $CH_3(CH_2)_{11}(OCH_2CH_2)_3OSO_3NH_4$.

3. The self-preserved pearlizing composition of claim 1, wherein the glycol compound comprises glycol distearate or glycol monostearate.

4. The self-preserved pearlizing composition of claim 1, wherein the betaine compound comprises cocamidopropyl betaine, lauramidopropyl betaine, lauryl betaine, coco betaine, cocamidopropyl hydroxysultaine, lauramidopropyl hydroxysultaine, or lauryl hydroxysultaine.

5. The self-preserved pearlizing composition of claim 1, wherein the composition has a pH of about 5.0 to about 7.0.

6. The self-preserved pearlizing composition of claim 1, wherein the salt comprises sodium chloride, ammonium chloride, or potassium chloride.

7. The self-preserved pearlizing composition of claim 1, wherein the solvent comprises water.

8. The self-preserved pearlizing composition of claim 1, consisting of:
an amount of about 15 to about 25 wt % of the glycol compound;
an amount of about 7 to about 15 wt % of the sulfate compound;
an amount of about 0.1 to about 1.0 wt % of the alcohol containing a $C_{12}$-$C_{24}$ alkyl group;
an amount of about 0.1 to about 1.0 wt % of the betaine compound;
an amount of about 0.1 to about 1.0 wt % of the salt; and
an amount of about 55 to about 75 wt % of the solvent, wherein the wt % is based on the total weight of the composition.

9. The self-preserved pearlizing composition of claim 1, wherein the composition has a solid content of about 25.0 wt % to about 40.0 wt % based on the total weight of the composition.

10. A personal care product comprising the self-preserved pearlizing composition of claim 1.

11. A method of preventing bacterial and/or fungal contamination in a personal care product, comprising: formulating the personal care product comprising a self-preserved pearlizing composition of claim 1.

* * * * *